(12) United States Patent
Henderson et al.

(10) Patent No.: US 11,033,022 B2
(45) Date of Patent: Jun. 15, 2021

(54) MICROMANIPULATION AND STORAGE APPARATUS AND METHODS

(71) Applicant: Genea IP Holdings Pty Limited, Sydney (AU)

(72) Inventors: Chester John Henderson, Preston (AU); Craig Matthew Lewis, Kew (AU); Tammie Kim Roy, Cammeray (AU); Eduardo Vom, Kew (AU)

(73) Assignee: Genea IP Holdings Pty Limited, Sydney (AU)

( * ) Notice: Subject to any disclaimer, the term of this patent is extended or adjusted under 35 U.S.C. 154(b) by 0 days.

(21) Appl. No.: 16/272,602

(22) Filed: Feb. 11, 2019

(65) Prior Publication Data
US 2019/0174743 A1  Jun. 13, 2019

Related U.S. Application Data

(60) Continuation of application No. 15/192,349, filed on Jun. 24, 2016, now Pat. No. 10,244,749, which is a
(Continued)

(51) Int. Cl.
*A01N 1/02* (2006.01)
*A61B 17/43* (2006.01)
(Continued)

(52) U.S. Cl.
CPC ......... *A01N 1/0284* (2013.01); *A01N 1/0263* (2013.01); *A01N 1/0268* (2013.01);
(Continued)

(58) Field of Classification Search
CPC .... A61D 19/04; A61D 19/025; A61D 19/022; A01N 1/0263; A01N 1/0284; A01N 1/0268; A61B 17/43; A61B 17/435
See application file for complete search history.

(56) References Cited

U.S. PATENT DOCUMENTS

| 4,683,058 A | 7/1987 | Lyman et al. |
| 5,026,342 A | 6/1991 | Hammerstedt et al. |

(Continued)

FOREIGN PATENT DOCUMENTS

| DE | 202006017103 U1 | 3/2007 |
| JP | 2002543041 A | 12/2002 |

(Continued)

OTHER PUBLICATIONS

Yun Seok Heo et al, Controlled loading of cryprotectants (CPAs) to oocyte with linear and complex CPA profiles on a microfluidic platform, Lab Chip, vol. 11, No. 1, Oct. 21, 2011, p. 3530, 15 pages, XP055284596.

(Continued)

*Primary Examiner* — Sean C. Barron
(74) *Attorney, Agent, or Firm* — Richard M. Goldberg

(57) ABSTRACT

An apparatus for micromanipulation of biological material, includes a vessel (1) having a reservoir (2) wherein the vessel has a channel (3) formed in a portion of the reservoir, the channel including an intermediate restriction (4) dimensioned to resist passage of the biological material but allow passage of liquid treatment solutions.

14 Claims, 9 Drawing Sheets

Related U.S. Application Data division of application No. 13/700,258, filed as application No. PCT/AU2011/000643 on May 27, 2011, now Pat. No. 9,374,995.

(60) Provisional application No. 61/349,296, filed on May 28, 2010.

(51) Int. Cl.
    *A61B 17/435*     (2006.01)
    *A61D 19/02*     (2006.01)
    *A61D 19/04*     (2006.01)

(52) U.S. Cl.
    CPC ............ *A61B 17/43* (2013.01); *A61B 17/435* (2013.01); *A61D 19/025* (2013.01); *A61D 19/04* (2013.01); *A61D 19/022* (2013.01)

(56) References Cited

U.S. PATENT DOCUMENTS

| | | | |
|---|---|---|---|
| 5,261,870 | A | 11/1993 | Hammerstedt et al. |
| 5,894,733 | A | 4/1999 | Brodner |
| 6,000,603 | A | 12/1999 | Koskenmaki et al. |
| 6,176,089 | B1 | 1/2001 | Bouche |
| 6,337,205 | B1 | 1/2002 | Wisniewski |
| 6,408,878 | B2 | 6/2002 | Unger et al. |
| 6,500,608 | B2 | 12/2002 | Forest et al. |
| 6,503,698 | B1 | 1/2003 | Dobrinsky et al. |
| 6,514,216 | B2 | 2/2003 | Inoue et al. |
| 6,519,954 | B1 | 2/2003 | Prien et al. |
| 6,717,182 | B1 | 4/2004 | Tagami et al. |
| 6,773,877 | B2 | 8/2004 | Fahy |
| 6,793,753 | B2 | 9/2004 | Unger et al. |
| 6,818,395 | B1 | 11/2004 | Quake et al. |
| 6,838,235 | B2 | 1/2005 | Gardner et al. |
| 6,899,137 | B2 | 5/2005 | Unger et al. |
| 6,911,345 | B2 | 6/2005 | Quake et al. |
| 6,929,030 | B2 | 8/2005 | Unger et al. |
| 6,982,172 | B2 | 1/2006 | Yang et al. |
| 7,040,338 | B2 | 5/2006 | Unger et al. |
| 7,052,545 | B2 | 5/2006 | Quake et al. |
| 7,087,370 | B2 | 8/2006 | Forest et al. |
| 7,094,601 | B2 | 8/2006 | Toner et al. |
| 7,144,616 | B1 | 12/2006 | Unger et al. |
| 7,169,314 | B2 | 1/2007 | Unger et al. |
| 7,195,670 | B2 | 3/2007 | Hansen et al. |
| 7,216,671 | B2 | 5/2007 | Unger et al. |
| 7,217,321 | B2 | 5/2007 | Hansen et al. |
| 7,244,402 | B2 | 7/2007 | Hansen et al. |
| 7,250,128 | B2 | 7/2007 | Unger et al. |
| 7,278,278 | B2 | 10/2007 | Wowk et al. |
| 7,306,672 | B2 | 12/2007 | Hansen et al. |
| 7,316,896 | B2 | 1/2008 | Kuwayama et al. |
| 7,326,296 | B2 | 2/2008 | Quake et al. |
| 7,435,582 | B2 * | 10/2008 | Zimmermann .......... A01N 1/02 435/307.1 |
| 7,459,022 | B2 | 12/2008 | Hansen et al. |
| 2001/0020636 | A1 | 9/2001 | Koskenmaki et al. |
| 2001/0029983 | A1 | 10/2001 | Unger et al. |
| 2001/0033796 | A1 | 10/2001 | Unger et al. |
| 2001/0054778 | A1 | 12/2001 | Unger et al. |
| 2002/0009704 | A1 | 1/2002 | Yang et al. |
| 2002/0025529 | A1 | 2/2002 | Quake et al. |
| 2002/0029814 | A1 | 3/2002 | Unger et al. |
| 2002/0144738 | A1 | 10/2002 | Unger et al. |
| 2002/0145231 | A1 | 10/2002 | Quake et al. |
| 2003/0019833 | A1 | 1/2003 | Unger et al. |
| 2003/0061687 | A1 | 4/2003 | Hansen et al. |
| 2003/0096310 | A1 | 5/2003 | Hansen et al. |
| 2003/0113706 | A1 | 6/2003 | Forest et al. |
| 2003/0124548 | A1 | 7/2003 | Hatzis et al. |
| 2003/0154729 | A1 | 8/2003 | Prien et al. |
| 2004/0000901 | A1 | 1/2004 | Sui |
| 2004/0115731 | A1 | 6/2004 | Hansen et al. |
| 2004/0259072 | A1 | 12/2004 | Kuwayama et al. |
| 2005/0014175 | A1 | 1/2005 | Quake |
| 2005/0062196 | A1 | 3/2005 | Hansen et al. |
| 2005/0106554 | A1 | 5/2005 | Palecek et al. |
| 2005/0112882 | A1 | 5/2005 | Unger et al. |
| 2005/0147992 | A1 | 7/2005 | Quake et al. |
| 2005/0166980 | A1 | 8/2005 | Unger et al. |
| 2005/0178317 | A1 | 8/2005 | Quake et al. |
| 2005/0205005 | A1 | 9/2005 | Hansen et al. |
| 2005/0226742 | A1 | 10/2005 | Unger et al. |
| 2005/0229839 | A1 | 10/2005 | Quake et al. |
| 2005/0250088 | A1 | 11/2005 | Boldt |
| 2006/0019263 | A1 | 1/2006 | Quake et al. |
| 2006/0046243 | A1 | 3/2006 | Stachecki et al. |
| 2006/0054228 | A1 | 3/2006 | Unger et al. |
| 2006/0134596 | A1 | 6/2006 | Sjogren et al. |
| 2006/0172408 | A1 | 8/2006 | Quake et al. |
| 2006/0177852 | A1 | 8/2006 | Gabbai |
| 2006/0188865 | A1 | 8/2006 | Fuhr |
| 2006/0196409 | A1 | 9/2006 | Quake et al. |
| 2006/0234204 | A1 | 10/2006 | Forest et al. |
| 2006/0246414 | A1 | 11/2006 | Chang et al. |
| 2007/0024903 | A1 | 2/2007 | Kitahara et al. |
| 2007/0037271 | A1 | 2/2007 | Huang et al. |
| 2007/0059494 | A1 | 3/2007 | Unger et al. |
| 2007/0087321 | A1 | 4/2007 | Pribenszky et al. |
| 2007/0169686 | A1 | 7/2007 | Quake et al. |
| 2007/0209572 | A1 | 9/2007 | Hansen et al. |
| 2007/0209574 | A1 | 9/2007 | Hansen et al. |
| 2007/0249038 | A1 | 10/2007 | Adamo et al. |
| 2008/0026460 | A1 | 1/2008 | Palecek et al. |
| 2008/0038155 | A1 | 2/2008 | Chian et al. |
| 2008/0050717 | A1 | 2/2008 | Brower, Jr. et al. |
| 2008/0050815 | A1 | 2/2008 | Sher et al. |
| 2008/0083177 | A1 | 4/2008 | Tiberi et al. |
| 2008/0220520 | A1 | 9/2008 | Palecek et al. |
| 2008/0236669 | A1 | 10/2008 | Unger et al. |
| 2008/0268492 | A1 | 10/2008 | Mullen et al. |
| 2009/0004296 | A1 | 1/2009 | Gabbai |
| 2009/0029340 | A1 | 1/2009 | Gabbai |
| 2009/0081305 | A1 | 3/2009 | Gabbai |
| 2009/0081782 | A1 | 3/2009 | Yoon et al. |
| 2009/0093054 | A1 | 4/2009 | Sjogren et al. |
| 2009/0120106 | A1 | 5/2009 | Chin |
| 2009/0123992 | A1 | 5/2009 | Chin |
| 2009/0123996 | A1 | 5/2009 | Chin |
| 2009/0126373 | A1 | 5/2009 | Burg |
| 2009/0130753 | A1 | 5/2009 | Bowermaster et al. |
| 2009/0186405 | A1 | 7/2009 | Chin |
| 2009/0202978 | A1 | 8/2009 | Shaham |
| 2009/0239207 | A1 | 9/2009 | Leese et al. |
| 2009/0253613 | A1 | 10/2009 | Gabbai |
| 2009/0255938 | A1 | 10/2009 | Fuja |
| 2009/0305224 | A1 | 12/2009 | He et al. |
| 2010/0015697 | A1 | 1/2010 | Junger et al. |
| 2010/0212331 | A1 | 8/2010 | Critser et al. |
| 2010/0267007 | A1 | 10/2010 | Gabbai |
| 2010/0281886 | A1 | 11/2010 | Shaham et al. |
| 2010/0297600 | A1 | 11/2010 | Cecchi |
| 2010/0317108 | A1 | 12/2010 | Stojanov |
| 2011/0207112 | A1 | 8/2011 | Burbank et al. |
| 2013/0137080 | A1 | 5/2013 | Henderson et al. |
| 2013/0204076 | A1 | 8/2013 | Han et al. |

FOREIGN PATENT DOCUMENTS

| | | |
|---|---|---|
| WO | 9908513 A1 | 2/1999 |
| WO | 00/21365 A1 | 4/2000 |
| WO | 02/085110 A1 | 10/2002 |
| WO | 2005/032341 A2 | 4/2005 |
| WO | 2006/097749 A1 | 9/2006 |

OTHER PUBLICATIONS

Li et al, Bulk vitrification of human embryonic stem cells, Human Reproduction, vol. 23, No. 2, Dec. 14, 2007, pp. 358-364.

Chen et al. Vitrification of mouse oocytes using closed pulled straws (CPS) achieves a high survival and preserves good patterns of

(56) References Cited

OTHER PUBLICATIONS meiotic spindles, compared with conventional straws, open pulled straws (OPS) and grids. Human Reproduction, 2001, V16(11), pp. 2350-2356.

Abe et al. Feasibility of a nylon-mesh holder for vitrification of bovine germinal vesicle oocytes in subsequent production of viable blastocysts. Biology of Reproduction, 2005, 72, pp. 1416-1420.

Matsumoto et al. Vitrification of large quantities of immature bovine oocytes using nylon mesh. Cryobiology, 2001, 42, pp. 139-144.

Park et al. Simple, efficient and successful vitrification of bovine blastocysts using electron microscope grids. Human Reproduction, 1999, vol. 14, No. 11, pp. 2838-2843.

Park et al. Ultra-rapid freezing of human multipronuclear zygotes using electron microscope grids. Human Reproduction, 2000, vol. 15, No. 8, pp. 1787-1790.

Dinnyes et al. High developmental rates of vitrified bovine oocytes following parthenogenetic activation, in vitro fertilization, and somatic cell nuclear transfer. Biology of Reproduction, 2000, 63, pp. 513-518.

Cryocane. www.coleparmer.com/buy/product/52491-thermo-scientific-cryocane-aluminum-300-fl-holds-6-vials-5015-0002.html#Specs; downloaded on Nov. 13, 2012, p. 1.

Cremades et al (2004). Experimental vitrification of human compacted morulae and early blastocysts using fine diameter plastic micropipettes. Human reproduction, v19(2), pp. 300-305.

Son and Tan (2009). Comparison between slow freezing and vitrification for human embryos. Expert Rev. Med. Devices, v6(1), pp. 1-7.

"Safe-Lock tubes 0.5 ml". (Nov. 13, 2009, captured from PDF properties). Product brochure by Eppendorf.

Daigger product brouch to "Racks/Liquid Measures" (Mar. 6, 2009). pp. 14-19 plus appended snapshot for pub. date.

Vutyavanich et al, Closed-system solid surface vitrification versus slow programmable freezing of mouse 2-cell embryos, J Assist Reprod Genet (2009) 26, pp. 285-290.

Rall et al, Development of mouse embryos cryopreserved by vitrification, J. Reprod.Fert. (1987) 80, pp. 499-504.

\* cited by examiner

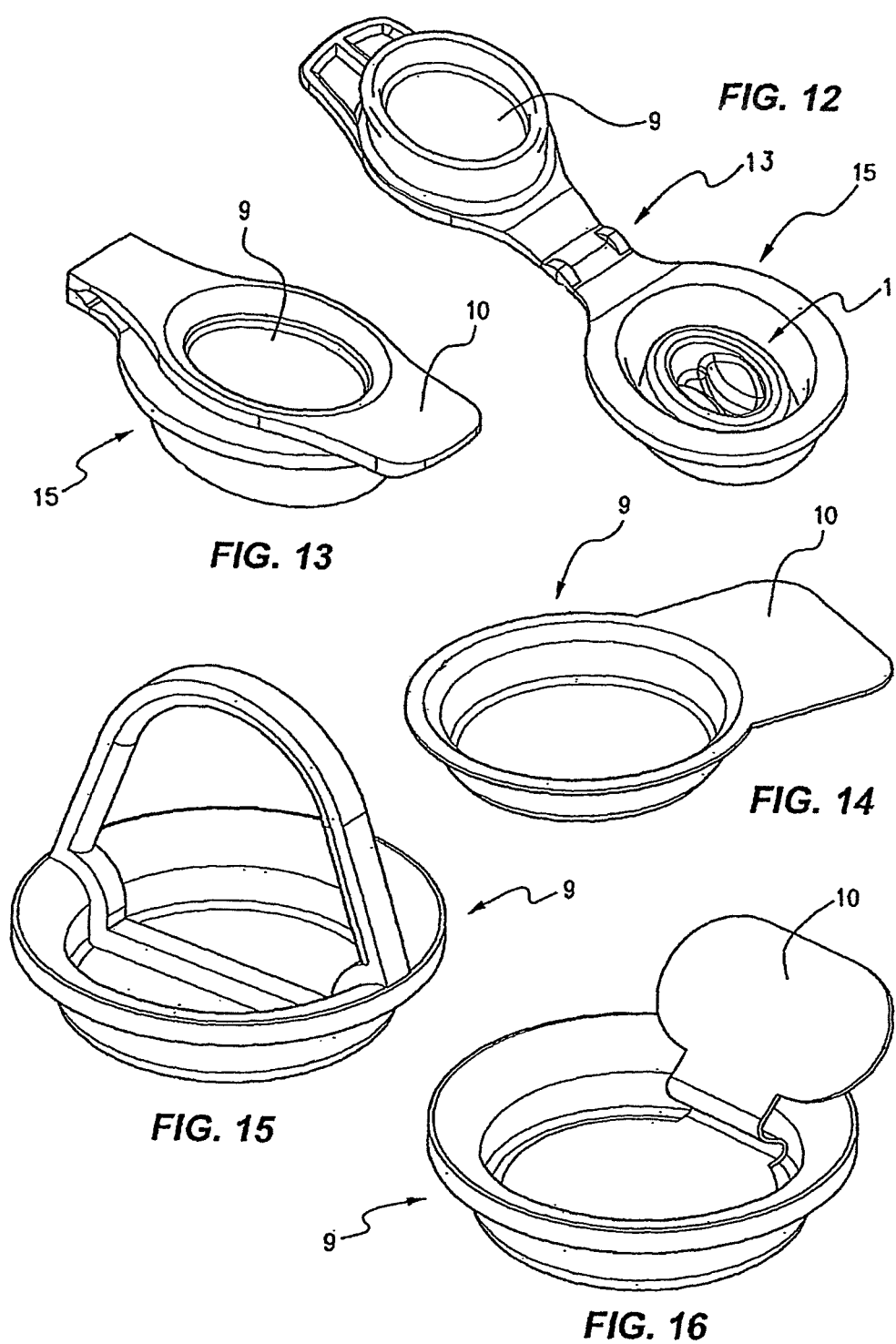

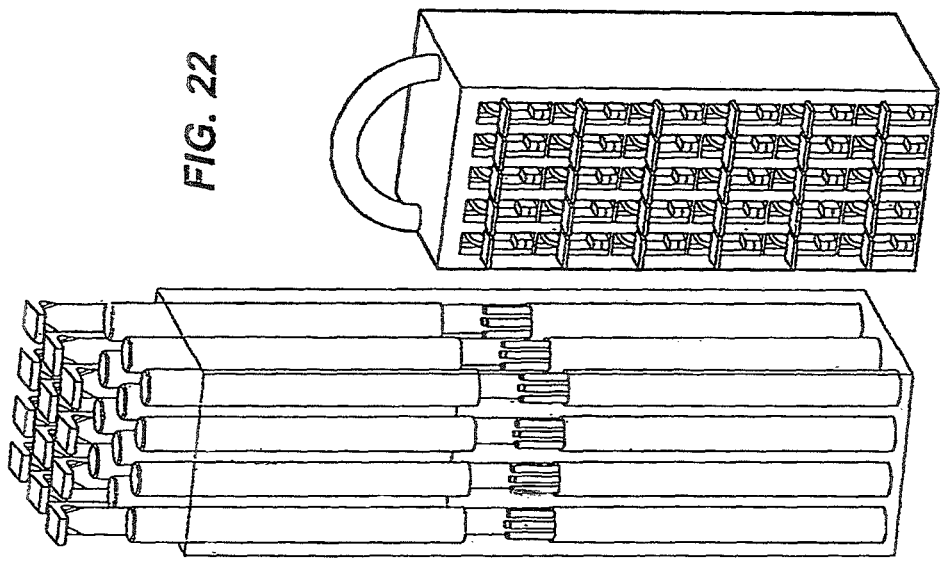
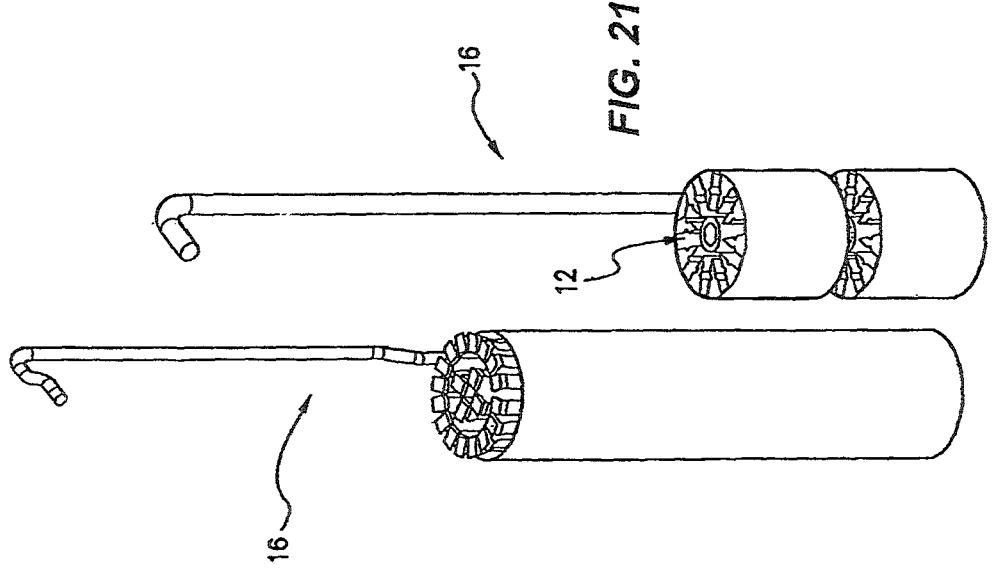

MICROMANIPULATION AND STORAGE APPARATUS AND METHODS

CROSS-REFERENCE TO RELATED APPLICATIONS

The present application claims priority from U.S. Provisional Patent Application No. 61/349,296 the content of which is incorporated herein by reference.

INTRODUCTION TO THE INVENTION

This invention relates to apparatus and methods for the micromanipulation of biological materials and in particular, apparatus and methodologies for use in the cryopreservation of biological materials including human and non-human oocytes, embryos, sperm, stem cells and blastocyst.

Whilst the invention has been developed and has application in a wide range of micromanipulation situations and techniques with a range of biological materials, it finds particular application for use in the cryopreservation of human oocytes, embryos, morula, sperm and stem cells by vitrification as applied during In Vitro Fertilisation (IVF) procedures and the like.

BACKGROUND OF THE INVENTION

The technologies involved and applied for cryopreserving of human and animal embryos are well established and with the application of suitable skill and know-how, the current technologies have achieved great improvement in the reliability and success in In Vitro Fertilisation procedures.

For the purposes of this specification, the term "freezing" and "vitrification" are taken to have the following definition:

"Freezing" is the cooling of a liquid to a solid state which may include crystalisation.

"Vitrification" is the cooling of a liquid to a solid state without crystalisation.

The techniques as understood and applied involve harvesting and cryopreservation of embryos, with a plurality of steps involving harvesting and extraction of oocytes, in vitro fertilisation thereof and the subsequent freezing and storing of such fertilised eggs and the resultant embryos and/or late stage blastocysts. The multitude of steps and handling stages required are heavily reliant on a high level of know-how and skill via the technical operators. The embryos or blastocysts once frozen, are then made available as required and can be thawed and transferred to the recipient whereby successful implantation to the uterus can result in normal development of a fetus and a resultant pregnancy.

More recently, such cryopreservation techniques have been successfully applied to unfertilised eggs and oocytes. Oocyte cryopreservation involves harvesting, freezing and storing of eggs or oocytes from a donor female in an unfertilised state. Such frozen eggs can then be drawn from a storage bank, thawed and made available for fertilisation and transferred to a donor on demand.

The techniques of cryopreservation as applied to oocytes rather than fertilised eggs and embryos, has certain ethical and medical advantages and has been subject to increased research and experimentation to improve the techniques involved.

The process of cryopreservation, particularly when applied to "live" biological materials, involves a high degree of trauma for the biological material in question, particularly having regard to the multiple handling steps required in accordance with current techniques. In addition to the trauma experienced as a result of physical handling, the biological material is also subject to potential ice crystal formation during freezing process, in addition to osmotic shock and toxic shock experienced during movement through a plurality of processing chemical solutions.

The traditional method of preparing frozen biological material includes the slow cooling of the material and its surrounding solution down to the storage temperature, with a view to deliberately initiating the formation of ice crystals remotely from the biological material per se. The traditional method is not optimal due to continuous formation of ice crystals. Alternative "vitrification" methods have been developed to address the ice crystal formation issues, however vitrification requires considerable technical skill for successful execution. Vitrification involves the transformation of the processing solution into a glass-like amorphous solid that is free from any crystalline structure, followed by extremely rapid cooling. The extremely rapid cooling is what enables the solution to achieve the glass-like amorphous state.

The application of either the traditional method of freezing or vitrification involves the use of chemical compounds and solutions, which are added to the biological material to minimise cell damage during the freezing processes. The chemical compounds and solutions are known as cryoprotectants and include permeating and non-permeating solutions. Permeating cryoprotectants are small molecules that readily permeate the membranes of the biological material with the formation of hydrogen bonds to the water molecules of the biological material with the aim of preventing ice crystallisation thereof. Examples of such permeating cryoprotectants are Ethylene Glycol (EG), Dimethyl Sulphoxide (DMSO) and Glycerol. At low concentrations in water, such permeating cryoprotectants lower the freezing temperature of the resultant solution and can assist in the prevention and minimisation of ice crystallisation. At higher concentrations which may differ at different cooling rates, such permeating cryoprotectants inhibit the formation of typical ice crystals and can lead to the development of a solid glass-like or vitrified state in which water is solidified prior to crystallisation or expansion. Toxicity of such permeating cryoprotectants increases with their increasing concentrations and is potentially toxic to the biological material in question and accordingly, the biological material must have minimal exposure to the permeating cryoprotectants over a very short period of time, or alternatively, exposure at a low temperature, whereby the metabolic rate of the biological material in question is reduced.

In contrast to the permeating cryoprotectants, the non-permeating cryoprotectants remain extracellular. Some examples of non-permeating cryoprotectants include disaccharides, trehalose and sucrose. The disaccharide cryoprotectants act by drawing free water from within the biological material and dehydrating the intracellular spaces. The resultant dehydration allows them to be used in combination with permeating cryoprotectants, such that the net concentration of the permeating cryoprotectant can be increased in the intracellular space. These techniques further assist the permeating cryoprotectant in preventing or minimising ice crystal formation.

During the vitrification process, permeating cryoprotectants may be added at a high concentration while the biological material's temperature is controlled at a predetermined level above freezing. However, because the toxicity of such high concentrations of permeating cryoprotectant can be substantial, it is not possible to retain the biological material at such temperatures for extended periods. Alternatively, a reduced time can be allowed for equilibrium after which the biological material, which may include oocytes or embryos are plunged directly into liquid nitrogen to effect freezing. The extremely rapid rate of cooling, minimises the negative effects of the cryoprotectant on the biological material and also, minimises ice crystal formation by encouraging vitrification.

The vitrification process involves exposing the biological material to at least three vitrification solutions. The vitrification solutions are typically added to successive wells in a multi-well culture dish, where the dish and solutions are warmed to a predetermined temperature, determined in accordance with the requirements of the biological material in question.

In a typical protocol, the biological material is physically transferred to a first solution in a first well and then washed by physically moving the biological material or cell through the solution in question with a cell pipetting device. The washing process is repeated in a second, third and fourth well over predetermined periods of time until the biological material or cell is considered ready for cryopreservation. The biological material is then physically drawn up with a predetermined amount of vitrification solution using a pipette or other handling device. A droplet containing the biological material or cell to be vitrified is then pipetted onto the vitrification device. The vitrification device is then physically transferred with the droplet and biological material attached and directly plunged into liquid nitrogen or placed onto the surface of a vitrification block that has been pre-cooled with liquid nitrogen. Once the biological material and the carrying fluid have become vitrified, the vitrification device is then inserted into a pre-chilled straw or other storage device, located in a slot in the vitrification block for subsequent transfer to long-term cold storage in either liquid nitrogen or liquid nitrogen vapour.

Various vitrification devices are used to manipulate the sample during the cryopreservation processes. Some propose a pipette style device in which the sample is sucked into a hollow tube which is then plunged directly into the solution or liquid nitrogen. Such device is marketed by Irvine scientific and sold as Cryotip®.

Other uses a loop/hook style device which will have a close loop or an open hook made from plastic or metal wire stuck to the end of a stem and is used to pick up the biological sample. Such devices are marketed by Cryologic under the trade name of fibreplug or Cryoloop as defined in WO00/21365.

Others tools as disclosed in international application WO 02/085110 "Cryotop" which is a flexible strip attached to a piece of plastic, in which the sample is placed on the strip and plunged directly into liquid nitrogen.

Current prior art requires many embryo handling steps using multiple apparatus; every handling step increases the chance of losing the embryo. It is estimated that 1-2% of embryos lost are contributed by handling during the vitrification step.

The trauma associated with the previously described processes and in particular the trauma imposed by repeated physical handing and manipulation of extremely delicate biological material including eggs, cells, embryos and blastocysts, impacts on the survival rate and hence the success, of the processes and methods previously described. Furthermore, the physical dynamics of a living embryo introduce rapid growing and changes to the shape of the embryo which further challenge any handling, and in particular, automated handling of such biological materials. Any automation needs to manage such dynamics as well as manage a range of different embryo types, rapid fluid movement along with a high range of fluid viscosities. Clearly, in order to maximise the chances of success and minimise trauma imposed on the materials being handled, it is highly desirable to reduce the physical handling of such delicate materials to an absolute minimum, in addition to minimising the number and degree of different washing solutions applied to the biological material.

Culturing is a technique to grow embryos to day 4, 5 or 6 post fertilisation to assist in the selection of the best quality embryos for transfer. Extended culture can increase the probability of a successful pregnancy.

One object of the invention is to provide improved apparatus and methods for the micromanipulation and storage of biological materials including but not limited to the culturing and cryopreservation of such materials.

Another object of the invention is to control the washing protocol times using automation and to reduce handling of the embryo, thus enabling full automation.

SUMMARY OF THE INVENTION

Detailed Description

In a first aspect the invention provides an apparatus for micromanipulation of one or more biological materials, said apparatus including a vessel having a reservoir wherein said vessel has a channel formed in a portion of said reservoir, said channel including an intermediate restriction dimensioned to resist passage of said biological material but allow passage of liquid treatment solutions. The restriction can include a generally vertical passage or a generally horizontal platform. The intermediate restriction may include a physical narrowing of the passage, an orifice partially blocking the channel or one or more divots or other partial blocking means. The liquid treatment solution can include culture medium, cryopreservation medium, thawing medium, vitrification medium, fertilisation medium, or buffer solution.

The vessel preferably has an open top with the channel formed at the bottom thereof. The channel most preferably includes sub-reservoirs at either end of the restriction. The vessel is preferably formed of a material with high thermal conductivity and diffusivity with a particular preference for high conductivity in the sub-reservoir and channel regions. The vessel preferably includes a cap or lid adapted to seal the open top as either a separate lid or an integral hinged lid.

The apparatus may include a holder for said vessel.

The vessel or holder preferably includes a portion adapted to receive a bar code or other indicia.

The vessel material is preferably chosen from a material capable, of being sterilised and is biologically inert so as to pose no threat of contamination to the biological material/s. The vessel material preferably has high thermal diffusion and most preferably is between 1 mm and 0.05 mm thick.

In another aspect the invention provides an apparatus being an automated cryopreservation device including provision for one or a plurality of the vessels as previously described wherein the apparatus further includes means to irrigate the captive biological material with vitrification and/or other treatment solutions and means to vitrify the captive biological material.

In another aspect the invention provides a semi automated device including provision for one or a plurality of the vessels as previously described wherein the apparatus includes a means to irrigate the captive biological material with pre-vitrification or vitrification treatment solutions and fluidics to prepare the captive biological material for vitrification.

In another aspect the invention provides a method of cryopreservation of biological material comprising the steps of:
introducing the biological material into one sub-reservoir region of the previously described vessel irrigating and draining the biological material with a series of vitrification solutions introduced and removed from the other sub-reservoir (at the other end of the channel from where the embryo is introduced)
final draining of said irrigation solutions from the vessel vitrifying the vessel and captive biological material.

In another aspect the invention provides a method of cryopreservation of biological material comprising the steps of:
introducing the biological material into one sub-reservoir region of the previously described vessel irrigating and draining the biological material with a series of vitrification solutions introduced and removed from the other sub-reservoir (at the other end of the channel from where the embryo is introduced)
dispensing minimal final vitrification solution
vitrifying the vessel and captive biological material.

The series of vitrification solutions preferably includes gradually increasing non-permeating and permeating cryoprotectants selected from Ethylene Glycol (EG), Dimethyl Sulphoxide (DMSO), Glycerol, disaccharides, trehalose and sucrose to enhance the sinking of said biological material to the bottom of said sub-reservoir region so as to allow maximum drainage and retention of minimal irrigation solution prior to vitrification or freezing.

In another aspect the invention provides a method for pre-vitrification treatment of a biological material said method comprising the steps of:
introducing said biological material into the reservoir region of an apparatus as previously described for capture in the channel region of said vessel;
irrigating and draining said biological material with culturing or pre-vitrification solutions and fluidics.

In another aspect the invention provides a method of thawing a vitrified biological material and method comprising the steps of:
withdrawing a vitrified biological material in an apparatus as previously described from cooling solution;
thawing the vessel and captive biological material by heating in a heated solution.
heat can also be applied to the surface of the vessel or surrounding air;
irrigating and draining said captive biological material with a series of thawing solutions introduced and removed from the reservoir region of said vessel;
draining said irrigation solutions;
recovering thawed biological material from said vessel.

In another aspect the invention provides a method of storing a cryopreservation biological material comprising the steps of:
introducing said biological material into the reservoir region of an apparatus as previously described for capture in the channel region or said vessel;
irrigating and draining said biological material with a series of vitrification solutions introduced and removed from the other sub-reservoir (at the other end of the channel from where the embryo is introduced);
final draining said irrigation solutions from said vessel;
vitrifying said vessel and captive biological material;
storing said vessel and captive biological material in a storage facility until the biological material is devitrified.

In another aspect the invention provides a method of thawing a frozen or vitrified biological sample comprising reversing the previously described method by using thawing solutions.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

LEGEND

1. Vessel
2. Reservoir
3. Channel
4. Restriction
5. Open top
6. Bottom
7. Sub-reservoirs
8. Channel ends
9. Cap or lid
10. Indicia platform
11. Support frame
12. Cassette
13. Hinge
14. Divot
15. Holder
16. Loader

BRIEF DESCRIPTION OF THE DRAWINGS

FIG. 12 shows the vessel holder with integral cap;
FIG. 13 shows the holder with cap closed;
FIG. 14 shows an alternative cap or lid;
FIG. 15 shows a cap or lid with a handle;
FIG. 16 shows a cap or lid with a peel-able opening.

FIG. 21 shows a Dewar storage loader;
FIG. 22 shows a tank storage system.

DETAILED DESCRIPTION OF THE INVENTION

Figure 1:
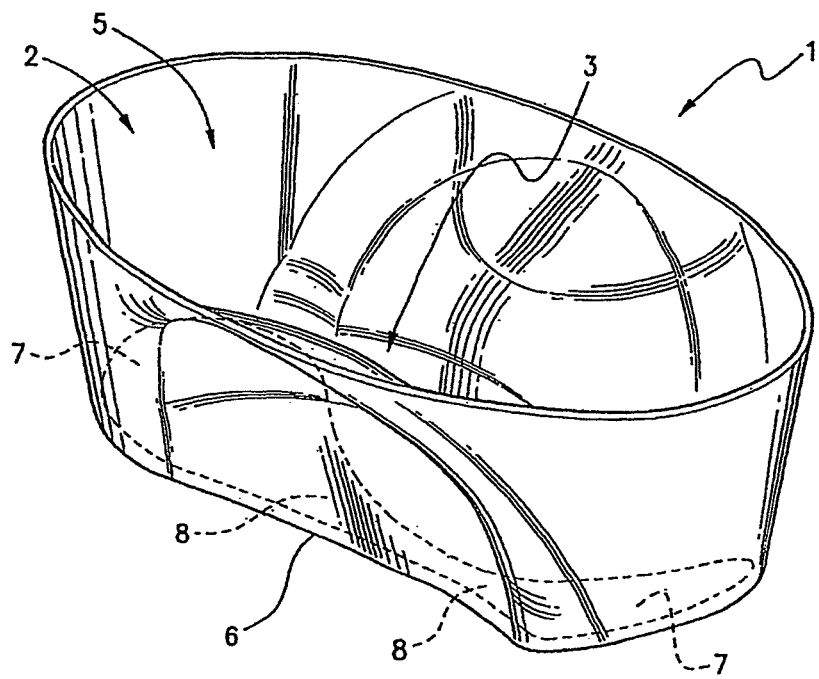
FIG. 1 shows a perspective view of the vessel.
Figure 2:
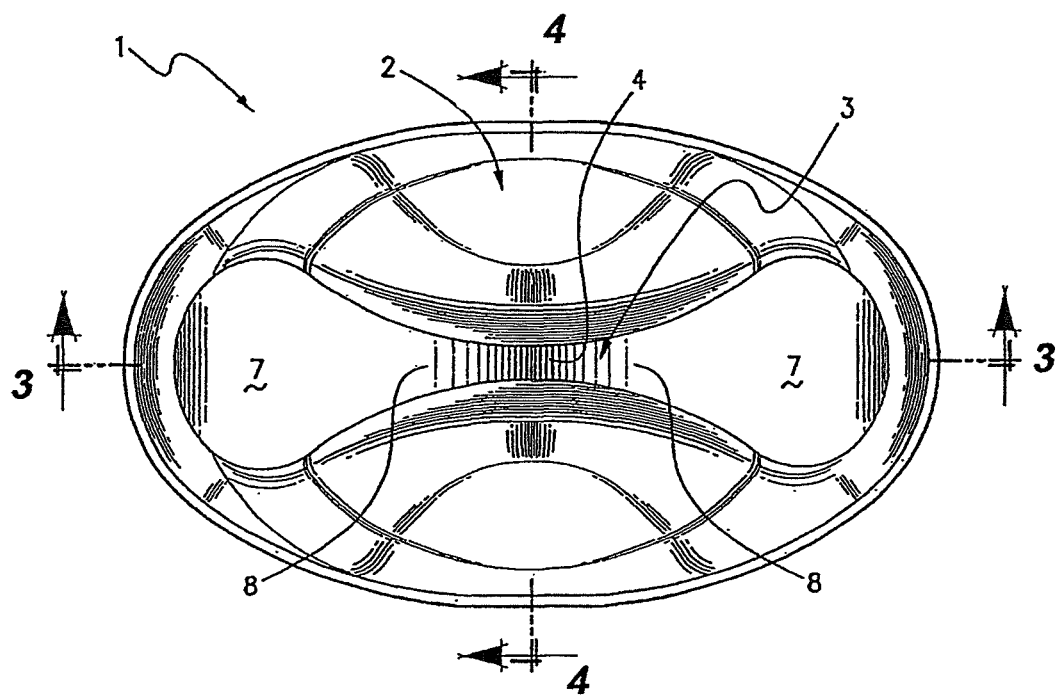
FIG. 2 shows a top view of the open vessel.
Figure 3:
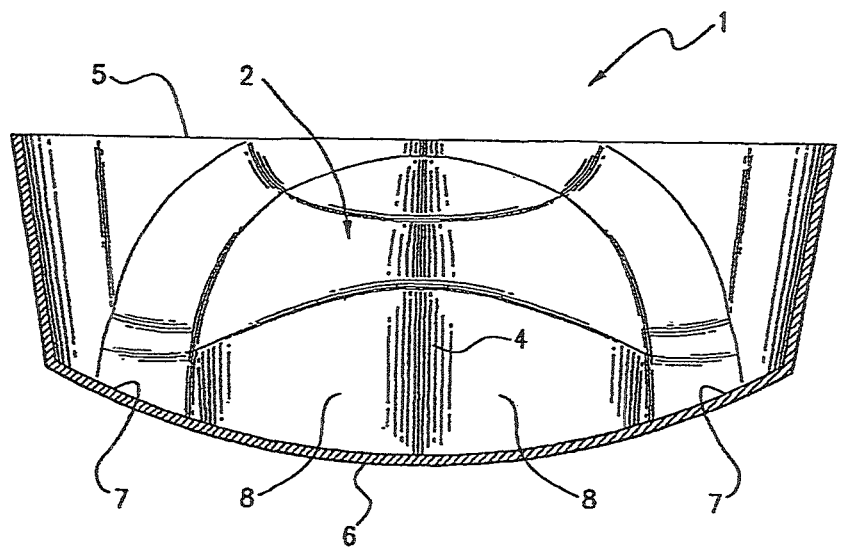
FIG. 3 shows a cross-sectional view of the vessel of FIG. 2, taken along line 3-3.
Figure 4:
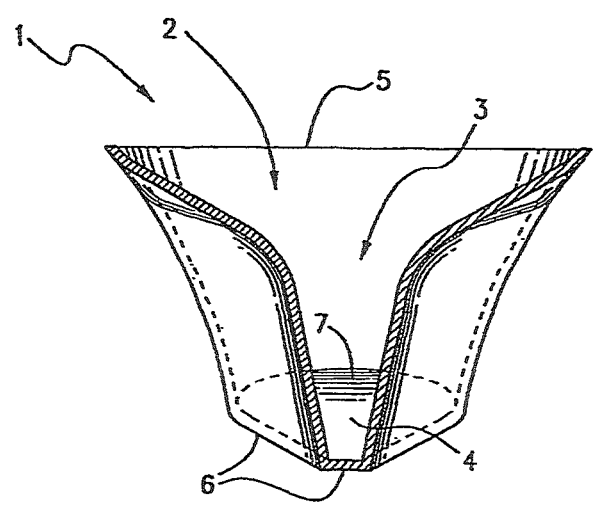
FIG. 4 shows a cross-sectional view of the vessel of FIG. 2, taken along line 4-4.
Figure 5:
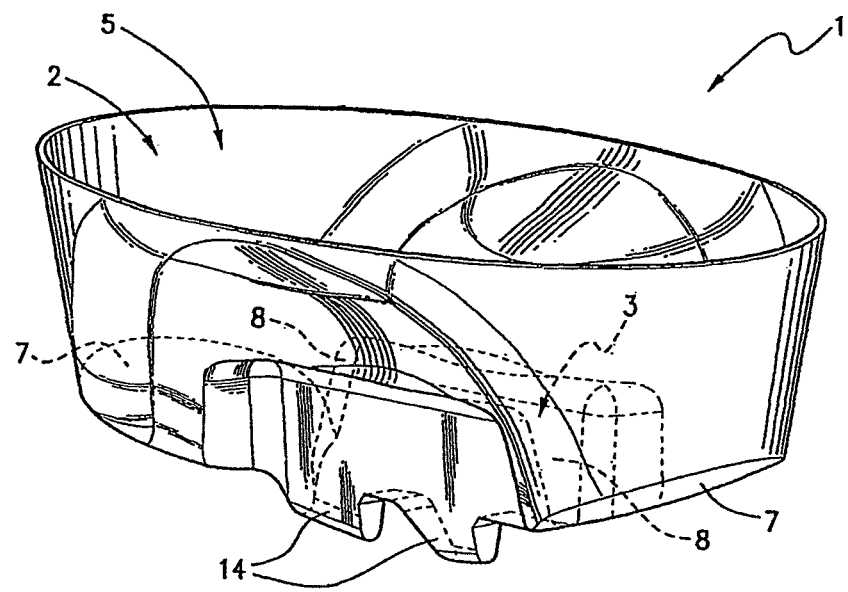
FIG. 5 shows a perspective view of the vessel with divots.
Figure 6:
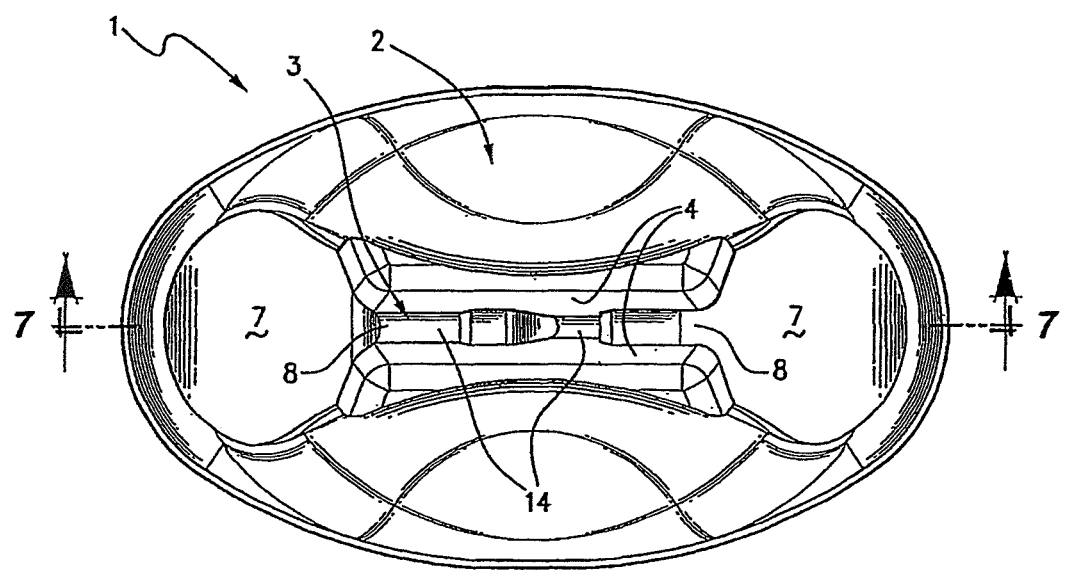
FIG. 6 shows a top view of the open vessel with divots.
Figure 7:
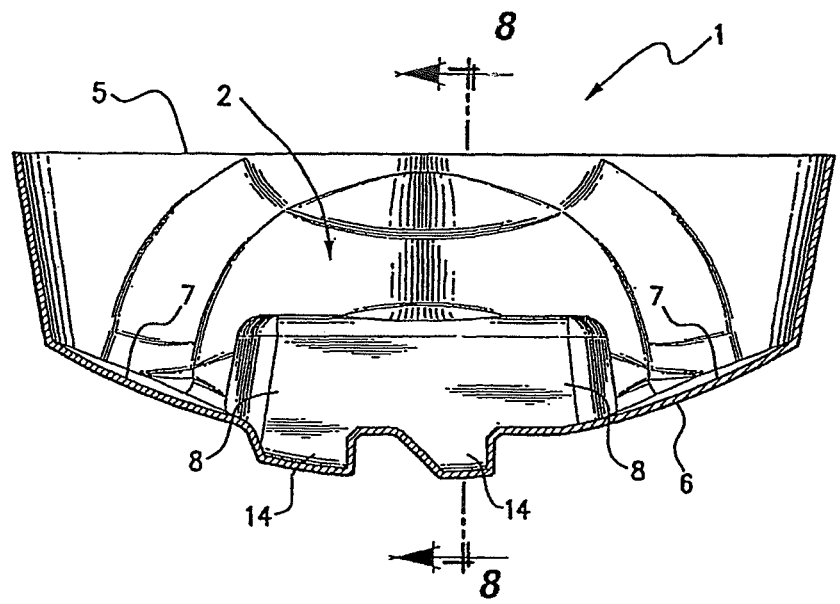
FIG. 7 shows a cross-sectional view of the vessel with divots of FIG. 6, taken along line 7-7.
Figure 8:
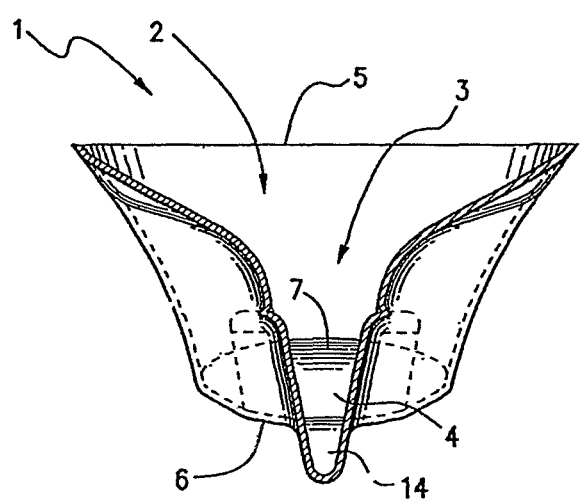
FIG. 8 shows a cross-sectional view of the vessel with divots of FIG. 7, taken along line 8-8.
Figure 9:
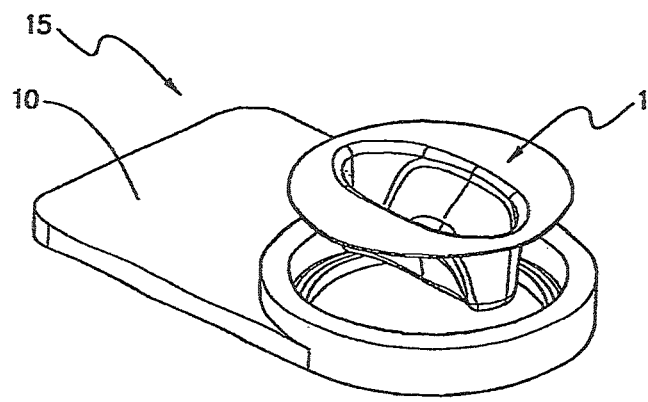
FIG. 9 shows the vessel and a holder.

The invention will now be described with reference to the Legend and Figures in the context of human in vitro fertilisation and the handling of biological material, being a fertilised human embryo, but the scope of the invention extends broadly to a wide range of micromanipulation techniques for biological material where the biological material in question can be conveniently handled and managed using the apparatus of the invention and made subject to a number of processing steps and procedures without being physically moved from the confines and security provided for by the apparatus of the invention.

In its broadest aspect, the invention provides a convenient holding vessel for receiving and securely holding a human embryo or other sample of biological material. The vessel 1 is formed as a unitary hollow bodied vessel having an internal reservoir 2. The vessel is preferably dimensioned to a small scale with the reservoir occupying the bulk of the vessel. The preferred small size of the vessel is particularly advantageous by allowing the miniaturisation and minimalisation of treatment solutions required for processing and vitrification of the biological material. The preferred volume for the treatment solutions is between 0.1 ul-100 ul, more preferably 0.5 ul-10 ul. The vessel preferably has an open top 5, giving direct access to the reservoir 2 with the open top providing ready access for introduction of the embryo or other biological material and also easy access for introduction and flushing of the treatment solutions being used.

The vessel is preferably generally oval in shape and includes a channel portion 3 formed in the bottom region 6 thereof. The channel region preferably includes dual raised portions of the bottom region 6 of the vessel which extend longitudinally and include a restriction 4 formed toward the centre thereof. In this manner, the integrally formed channel provides a preliminary flow path for introduced treatment solutions which can be introduced into the reservoir and flushed along the channel from one end 8 to the other end 8. As more treatment solution is introduced into the reservoir the flew path moves over the channel into the bulk of the reservoir. The provision of the channel creates two sub-reservoirs 7 at either end of the vessel, communicating with and being formed integrally to the channel. The channel has a restriction 4 at or near the middle or centre thereof, which is dimensioned to resist passage of a human embryo or resist passage of whatever biological material intended for use. The restriction is most preferably dimensioned to resist, but not totally prohibit passage of a human embryo, but dimensioned to encourage the human embryo to remain within one of the sub-reservoirs where the action of surface tension and fluid dynamics encourages the embryo to remain at one or other of the sub-reservoirs, rather than moving from one sub-reservoir to the other as treatment liquids are flushed into the reservoir, and through the channel.

As fluid is drawn through the channel away from the sub-reservoir containing the embryo, the dimensions and cross-section of the channel restrict fluid movement in a particular region in the manner of a "dead pocket". This region is on the base of vessel, in the vicinity of the gradual transition of wider sub-reservoir to narrower channel. This configuration allows the captive embryo to be retained at one end and minimises treatment solution needed to flush the embryo.

The reservoir is preferably symmetric—when the fluid withdrawal position is further away from the centreline of the channel than the restricted flow region described above (i.e.—actually in the sub-reservoir), the surface tension retaining fluid in the channel overcomes the surface tension joining the fluid to the withdrawal position as it is further away. The fluid eventually 'breaks', leaving a residual volume in the channel, containing the embryo. The residual volume is sufficiently small for rapid vitrification of the embryo.

The geometry of the holding vessel contributes to the flow characteristics of fluid movement and contribute toward control and manipulation of the embryo. For example, withdrawal of fluid too close to the channel, will risk draining the channel totally and loosing the embryo. Conversely, if fluid is withdrawn too far away from the channel, too much fluid can be left behind which can compromise rapid vitrification. Moreover, the rate of fluid withdrawal is important to ensure there is a "dead pocket".

The floor of the sub-reservoirs preferably slope towards the channel to enable gravity to assist locating the embryo in the "dead pocket". The slope should preferably not continue into the channel, but most preferably has a flatter base to prevent the embryo from entering the channel proper.

Referring to FIGS. 5 to 8, in a particularly preferred embodiment the "dead pocket" can be provided by way of the provision of one of more divots 14 formed in the intermediate restriction 4, wherein the divots 14 comprise one or more minor indentations, dimensioned to capture the biological material or embryo within a small pocket within the intermediate restriction 4. In this manner, the divots 14 provide a number of advantages including the provision of a fixed and specific location for the end user to position the biological material inserted into the apparatus of the invention. The divot 14 provides a specific location and helps ensure the biological material ends up being positioned in a highly specific location during the operation of fluid exchange. The divot 14 further provides a barrier to prevent the embryo or biological material from being aspirated away. The provision of two divots allows asymmetrical positioning where a first divot is positioned the start of the restriction and a second divot positioned at the middle of the restriction.

In addition, the provision of a divot 14 allows for maximum removal of previous irrigation solutions and in particular, the divot 14 allows a highly controlled volume of leftover solution surrounding the captured biological material or embryo and therefore allows the reliable dispensation of a minimal amount of vitrification solution whilst knowing the precise position of the embryo of biological material within the apparatus.

Diameter of the withdrawal tip may contribute to the fluid bridging between the sides of the sub-reservoir and assisting fluid removal and flow patterns.

In this manner, the vessel of the invention provides for the highly controlled handling and manipulation of human embryos and the like, where the human embryo can be carefully placed into the vessel at one or other of the sub-reservoirs 7 or directly into the divot. Once the embryo is carefully positioned in the sub-reservoir or divot, the treatment fluids can be then carefully introduced into the vacant sub-reservoir which is not occupied by the biological material and with the gentle flushing of fluid from an unoccupied or vacant sub-reservoir through the channel to the occupied sub-reservoir, the treatment fluids can be withdrawn and the subsequent treatment fluids are then introduced into the unoccupied sub-reservoir and gently flushed through to the occupied sub-reservoir. In this manner, a plurality of flushing operations can be executed with minimal disturbance of the embryo which is held captive in the occupied sub-reservoir or divot using the vacant sub-reservoir to add or withdraw fluids.

In a particularly preferred embodiment, the treatment fluids can be graduated such that one continuous flushing operation can be executed using a gradation of treatment fluids so as to minimise trauma and toxic shock to the embryo held captive in a first sub-reservoir. In this way, the embryo is subject to only one act of physical flushing, thereby greatly minimising any disturbance of the embryo. The configuration of the channel and restrictions is adapted to encourage flushing of fluids therethrough, whilst minimising any unnecessary turbulence which could potentially buffet and physically damage the embryo held captive in the first sub-reservoir.

The treatment fluids preferably contain gradually increasing non-permeating cryoprotectants and permeating cryoprotectants selected from Ethylene Glycol (EG), Dimethyl Sulphoxide (DMSO), Glycerol, disaccharides, trehalose and sucrose which are specifically adapted to enhance or encourage the sinking of the embryo or biological material to the bottom of the vessel. This enhances maximum drainage from the vessel and retention of minimal irrigation solution prior to vitrification or freezing, thereby enhancing the vitrification or freezing step. In addition, by ensuring the biological sample the embryo rapidly sinks to the bottom of the vessel, the chances of the biological material or embryo inadvertently escaping the vessel is minimised.

The vessel is preferably formed of a material having a high degree of thermal diffusivity to ensure fast cooling rate. In addition, the material forming the vessel is preferably biologically inert to minimise any possible contamination of the biological material. When the treatment liquids have all been removed, the vessel is adapted for vitrifying by placement in liquid nitrogen or the like, such that the captive embryo is itself vitrified rapidly by the high thermal conductivity and diffusivity of the vessel materials. In this way, the positioning of the embryo in the sub-reservoir at the bottom of the vessel, allows the vessel to be placed in liquid nitrogen, such that the liquid nitrogen has maximum thermal transmission directly to the embryo, whilst quarantining the embryo from any direct contact with the liquid nitrogen or other vitrification medium per se. Once the vitrification process is accomplished, the vessel and captive (now vitrified) embryo, can be removed from the liquid nitrogen and the vessel stored in a vitrified state awaiting thawing and use of the captive embryo, or alternative biological material.

An additional advantage of the vessel of the invention, particularly the vessel including the optional provision of divots and the minimal vitrification fluid used in the cooling process involves thawing, where thawing of the frozen biological material within the vessel of the invention can be accomplished rapidly with minimal disruption, due to the minimal amount of solution surrounding the biological material as achieved by the provision of the small divot or divots. The staled vessel of the invention can be placed directly into a warm, solution to achieve rapid and controlled thawing whilst maintaining maximum viability of the biological sample.

The vessel may be provided with a dedicated holder 15 as shown in FIGS. 9 to 13.

In order to maximise the versatility of the vessel and apparatus of the invention, the vessel and/or holder are preferably provided with a cap or lid 9, variations of the cap or lid being shown in FIGS. 14 to 16. The lid can be formed as a separate item or hinged directly and is adapted for snug fit to the open top 5 region of the vessel 1 and is most preferably adapted to cooperate with the channel formation so as to snap-fit and close the reservoir and provide minimal open space within the closed vessel. The provision of a lid assists in the handling and manipulation of the vessel, particularly when it is placed into liquid nitrogen and subsequently vitrified and stored for future use. The lid also protects the vitrified embryo from contamination and damage whilst in the vitrified state.

The lid is preferably formed integral to the vessel holder as shown in FIGS. 12 and 13 by way of an integral hinge 13 formed between the body of the vessel 1 or holder 15 and the lid 9. In this manner, the vessel is formed as a one-piece item thereby minimising the need to locate and provide a separate seal for the vessel and provides a ready means of sealing and closing the vessel immediately at hand.

Figure 10:
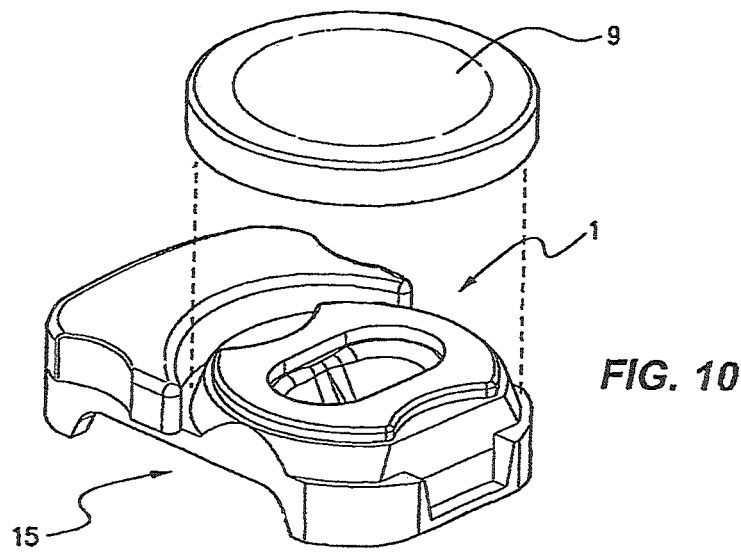
FIG. 10 shows an alternative holder and cap.
Figure 11:
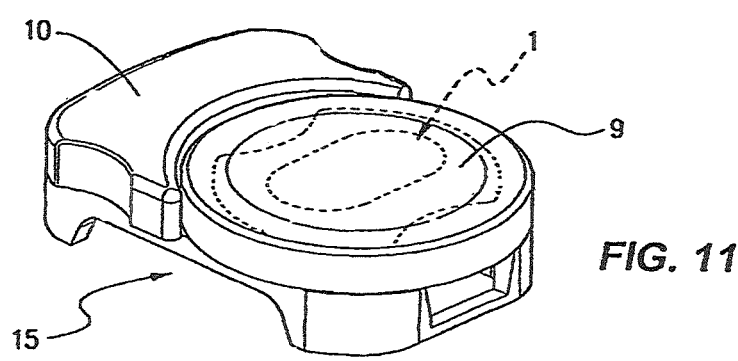
FIG. 11 shows the cap fitted to the vessel in the holder.
Figure 17:
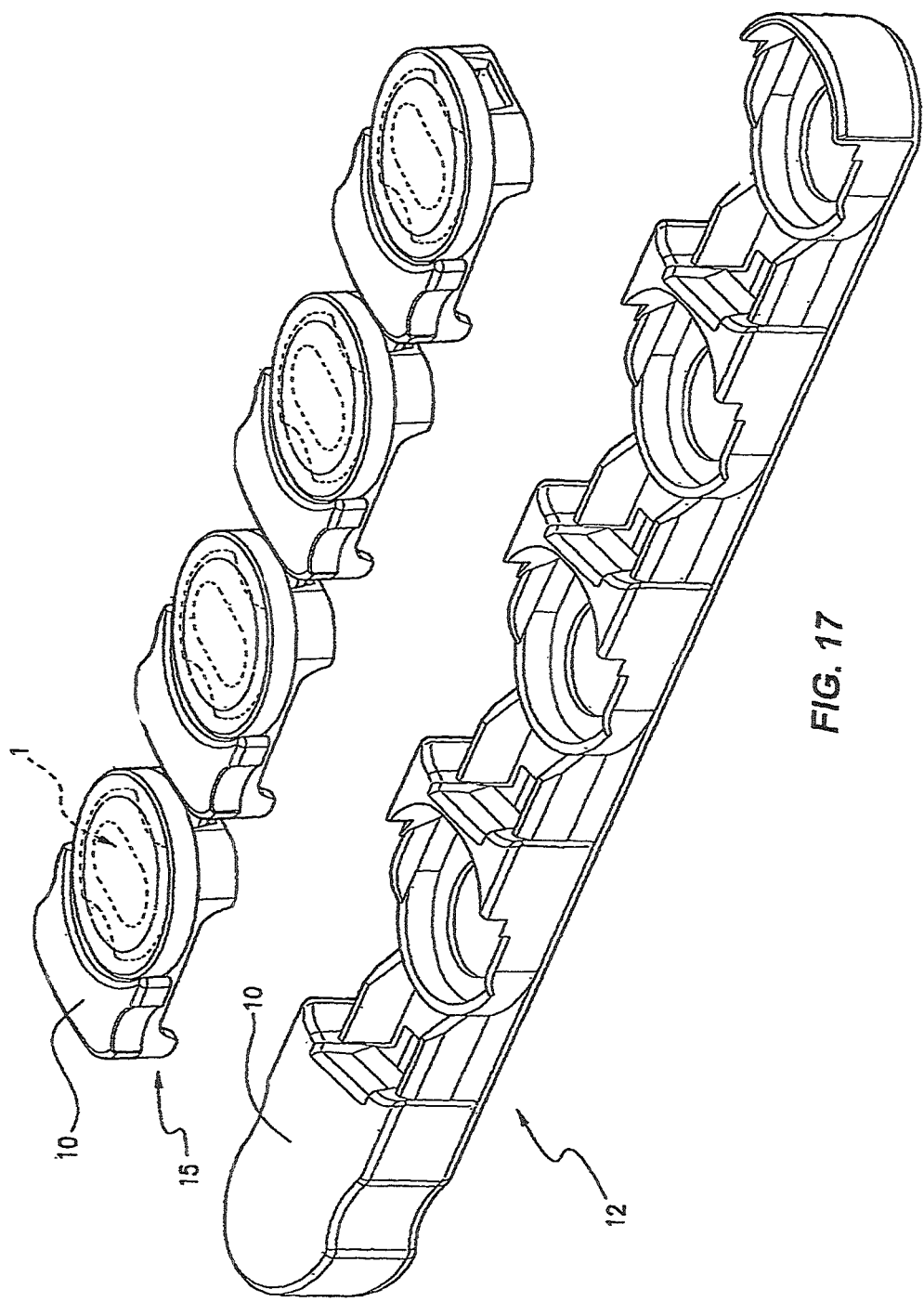
FIG. 17 shows a holder and vessel cassette.

Sealing can be either mechanical seal as describe above or chemical heat seal as shown in FIGS. 10 and 11.

The apparatus of the invention also includes a physical region thereof for the provision of a bar code or other identifying indicia whereby the indicia platform 10 allows the ready and secure identification of the vitrified embryo or other item of biological material. The vessel thereby provides maximum security and identification for a given human embryo, particularly as the biological material in question undergoes effectively one handling step only during the whole process post harvesting, through to vitrification and thawing. In this manner, the embryo has little or no chance of being mislabelled or misidentified during multiple steps and processes required for preparation and vitrification as the embryo never leaves the confines of the vessel once the treatment commences.

In another aspect the invention provides a cryopreservation apparatus where reference to FIGS. 17 to 21 details the adaptation of the vessel 1 of the invention which can be provided with a cassette 12, adapted to hold a plurality of sealed vessels. The cassette is preferably designed to accept open vessels and to be used throughout the vitrification process from start to end. Up to 4 vessels can be placed in the cassette prior to processing, once the biological material is irrigated with the vitrification solution, the lid can be closed/heat sealed and plunged into liquid nitrogen. In another aspect the cassette is designed to receive sealed vessels once the embryos have been processed and vitrified and subsequently sealed into the closed vessels as previously described. A plurality of vessels in the cassette are subsequently placed in a Canister which is then stored in a Dewar storage facility as detailed in FIG. 21 or alternative storage. The cassette preferably includes a portion adapted to receive a bar code or other indicia 10.

Figures 18, 19, 20:
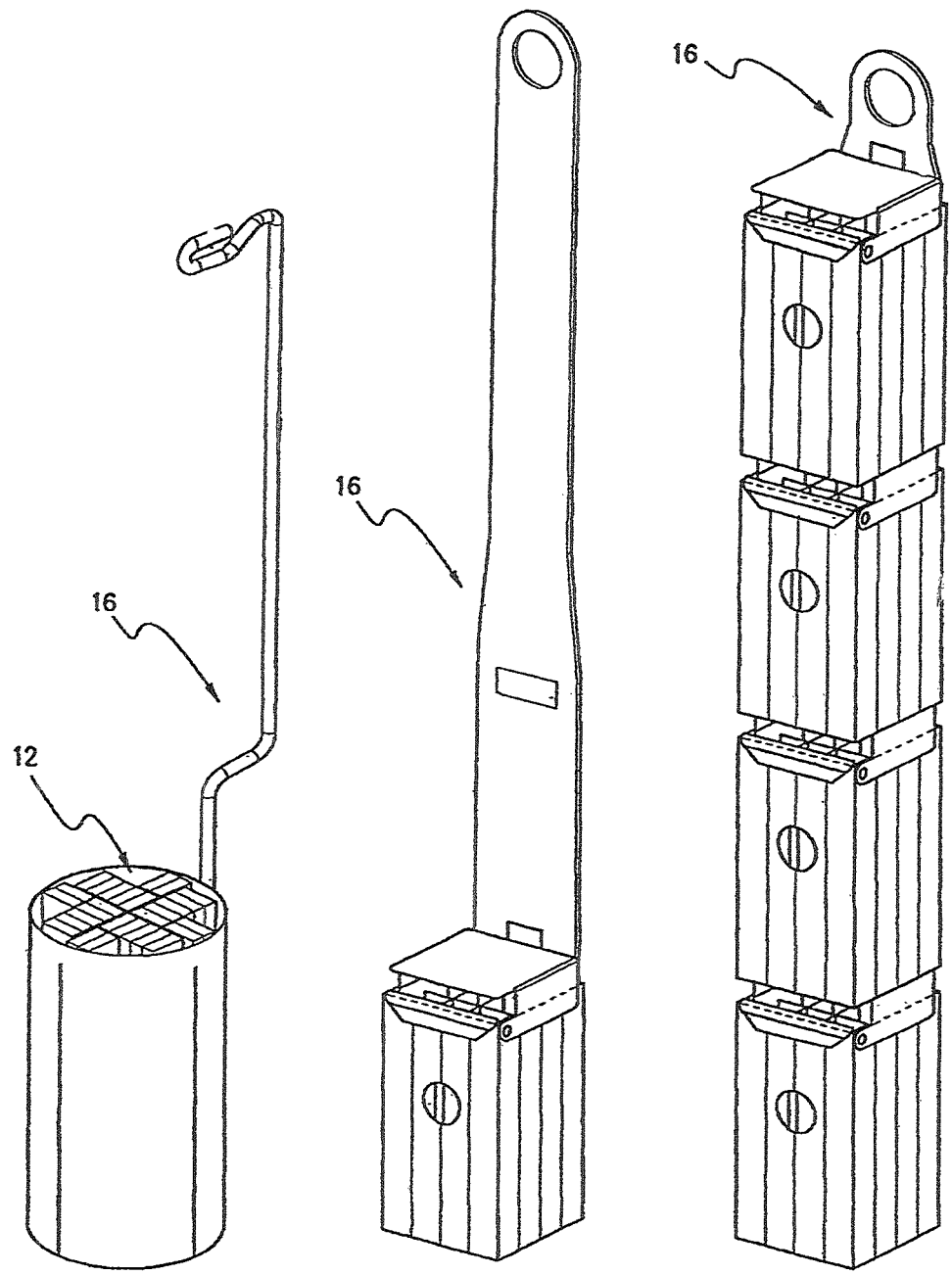
FIG. 18 shows a storage loader.
FIG. 19 shows an alternative storage loader.
FIG. 20 shows a stacked loader.

The cassettes are adapted for placement in a loader 16 as shown in FIGS. 18 to 20 with the current storage system is shown in FIG. 21.

An alternative storage is shown in FIG. 22, being a tank storage concept.

The tank storage concept has advantages over current systems by:
　Increasing capacity of samples being able to store
　Easier retrieval by large identification areas located on both the cassette and vessel
　Partitioned to allow both cassettes and vessels to be located in a fixed position The apparatus and in particular the vessel component of the invention lends itself to automation where the vessels can be automatically handled by suitable automated apparatus such that the array of vessels provided in an automated example of the invention, can, once the embryos have been carefully positioned into the vessel, then allow the full automation of the vitrification/freezing preparations and vitrification/freezing steps and the subsequent vitrifying/freezing and storage of a plurality of embryos to be fully automated without the requirement for the embryo to be moved, or requirement for individual monitoring or handling during any of the subsequent steps.

In another aspect the invention provides a semi automated device including provision for one or a plurality of the vessels as previously described wherein the apparatus includes a means to irrigate the captive biological material with pre-freezing or vitrification treatment solutions and fluidics to prepare the captive biological material for vitrification.

The vessel of the invention also finds various other uses including:
- irrigation said biological material with culturing media (culturing);
- irrigation said biological material with vitrification solutions;
- vitrifying said vessel and captive biological material;
- storage;
- thawing said vessel;
- irrigation said biological material with thawing solution.

The full automation of the in vitro fertilisation preparation of vitrified embryos is expected to provide substantial improvements to viability of the rendered embryos, thereby maximising the viability of embryos once thawed and consequently maximising the chance of success and pregnancy to recipients of embryos provided by way of the apparatus and methods of the invention.

In addition to the apparatus the invention also provides a range of methods for the handling of biological materials as described.

In another aspect the invention provides a method of cryopreservation of biological materials comprising the steps of introducing a selected biological material into the reservoir region of a vessel as previously described for capture in the channel region thereof;
- irrigating and draining said biological material with a series of vitrification solutions introduced and removed from the other sub-reservoir (at the other end of the channel from where the embryo is introduced);
- final draining said irrigation solutions from said vessel;
- vitrifying said vessel and captive biological material;

In the most particularly preferred embodiment where the apparatus includes the optional provision of one or a plurality of divots positioned within the intermediate restriction a typical protocol would consist of moving the embryo of biological material from a series of vitrification media to the final and most active solution. The media composition and time spent in each solution may be as follows:

| Media | Time spent in solution |
| --- | --- |
| Solution 1: "Cryobase" Basic solution | 1-15 minutes |
| Solution 2: "Vitrification solution 1" Media with 7-10% of DMSO and EG | 3-12 minutes |
| Solution 3: "Vitrification solution 2" Media with 15-18% DMSO and EG plus non permeating cryoprotectants. | 30 sec to up to 3 minute |

Listed below are examples of variations in protocol of cryopreservation of biological material using the described apparatus.

Protocol Example 1

Protocol of cryopreservation of biological material comprising of:
1. Introducing said biological material into the reservoir region of the vessel with cryobase.
2. The cryobase is drained from the aspirate/dispense position.
3. Vitrification solution 1 is dispensed filling the entire channel.
4. The biological material is then allowed to equilibrate in vitrification solution 1.
5. Vitrification solution 1 is drained from the aspirate/dispense position, leaving minimal amount of vitrification solution 1.
6. Vitrification solution 2 is dispensed filling the entire channel.
7. The biological material is then equilibrated for a very short time.
8. Vitrification solution 2 is drained from the aspirate/dispense position leaving minimal amount of vitrification solution 2.
9. The vessel and the biological material are then vitrified in liquid nitrogen.

Protocol Example 2

An alternative protocol is provided, without the removal of vitrification solution 2 as follows:
1. Biological material is placed into the vessel directly into the divot with cryobase.
2. The cryobase is drained from the aspirate/dispense position.
3. Vitrification solution 1 is dispensed into and filling the entire channel.
4. The biological material is then allowed to equilibrate in vitrification solution 1, the vessel is dimensioned so that the biological material will roll back into the divot.
5. Vitrification solution 1 is drained from the aspirate/dispense position, leaving minimal amount of vitrification solution 1 in the divot.
6. Small volume of vitrification solution 2 (between 0.5 ul-2.5 ul) is dispensed into the channel covering both the divot and biological material.
7. The biological material is then equilibrated for a very short time.
8. The vessel and the biological material are then vitrified in liquid nitrogen.

Protocol Example 3

In addition, a protocol involving the addition of non-permeating cryoprotectant to the cryobase/vitrification solution 1, is provided as follows:
1. Biological material is placed into the vessel directly into the divot with cryobase.
2. The cryobase is drained from the aspirate/dispense position.
3. Vitrification solution 1 is dispensed into and filling the entire channel.
4. The biological material is then allowed to equilibrate in vitrification solution 1, the vessel is dimensioned so that the biological material will roll back into the divot.
5. Vitrification solution 1 is drained from the aspirate/dispense position, leaving minimal amount of vitrification solution 1 in the divot.

6. Vitrification solution 2 is dispensed into the channel covering the entire channel.
7. The biological material is then equilibrated for a very short time.
8. Vitrification solution 2 is drained from the aspirate/dispense position, leaving minimal amount of vitrification solution 2 in the divot.
9. The vessel and the biological material are then vitrified in liquid nitrogen.

Protocol Example 4

In addition, a protocol involving a single vitrification solution gradually added, is provided as follows:
1. Biological material is placed into the vessel directly into the divot with cryobase.
2. The cryobase is drained from the aspirate/dispense position.
3. Single vitrification solution is gradually introduced into the sub-reservoirs and filling the entire channel.
4. The biological material is then allowed to equilibrate in vitrification solution, ensuring the biological material sinks to the bottom and remains in the divot or the intermediate restriction.
5. Vitrification solution is drained from the aspirate/dispense position, leaving minimal amount of vitrification solution.
6. The vessel and the biological material are then vitrified in liquid nitrogen.

In another aspect the invention provides a method for pre-vitrification treatment of a biological material, said method comprising the steps of:
introducing said biological material into the reservoir region of the apparatus as previously described for capture in the channel region of said vessel;
irrigating and draining said biological material with culturing for pre-vitrification solutions and fluidics.

In another aspect the invention provides a method of thawing a vitrified biological material, said method comprising the steps of:
withdrawing a biological material vitrified in an apparatus as previously described from cooling solution;
thawing the vessel of said apparatus and said biological material by application of heat in a heated solution, applying heat to the surface of the vessel or applying heat to the surrounding area of said vessel;
irrigating and draining said captive biological material with a series of thawing solutions introduced and removed from the reservoir region of said vessel;
draining said irrigation solutions;
recovering thawed biological material from said vessel.

In a further aspect the invention provides a method of storing a cryopreservation biological material comprising the steps of:
introducing said biological material into the reservoir region of an apparatus as previously described for capture in the channel region of said vessel;
irrigating and draining said biological material with a series of vitrification solutions introduced into the first of said sub-reservoirs and removed from the second of said sub-reservoirs;
a final draining of said irrigation solutions from said vessel;
vitrifying said vessel and captive biological material;
storing said vessel and captive biological material in a storage facility until the biological material is devitrified.

The methods of the invention lend themselves to a high degree of automation where the methods can be executed in automated apparatus and devices such that a plurality of embryos or other biological material can be processed simultaneously. The particular features of the invention allow for a high number of embryos or other biological material samples to be manually introduced into the vessels of the invention.

Once the individual samples of biological material have been introduced into a dedicated vessel and the vessels installed in the automated apparatus as previously described, the whole process of preparation for vitrification can be totally automated and monitored such that a large number of biological samples can be competently processed and vitrified in a seamless single-step operation.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive:

What is claimed is:
1. An apparatus for micromanipulation of at least one biological material, said apparatus including a vessel defining:
a reservoir with an open top;
a channel formed at a bottom of the reservoir opposite the open top;
a first sub-reservoir at a first end of the channel; and
a second sub-reservoir at a second end of the channel,
wherein the open top extends from the first sub-reservoir to the second sub-reservoir, and
wherein the channel narrows between the first and second sub-reservoirs to form an intermediate restriction dimensioned to resist passage of said biological material but allow passage of liquid treatment solutions.
2. An apparatus according to claim 1, wherein said intermediate restriction is dimensioned to resist passage of an embryo but allow passage of liquid treatment solutions.
3. An apparatus according to claim 1, wherein said vessel defines gradual transitions between the intermediate restriction and the sub-reservoirs which are relatively wider than the intermediate restriction.
4. An apparatus according to claim 1, wherein a floor of each sub-reservoir slopes down towards the channel at the bottom of the vessel.
5. An apparatus according to claim 1, wherein said vessel is formed of a thermally diffusive material.
6. An apparatus according to claim 1, wherein said vessel optimises heat transfer in the region of said sub-reservoirs and channel.
7. An apparatus according to claim 1, including one of a cap and lid adapted to seal the open top of said vessel.
8. An apparatus according to claim 1, including a portion adapted to receive at least one of a bar-code and other indicia.
9. An apparatus according to claim 1, wherein the restriction is defined by convex surfaces of side walls of the channel.
10. An apparatus according to claim 9, wherein the convex surfaces are curved in a first direction over at least part of a length of a channel, and curved in a second direction over at least part of a depth of the channel.
11. An apparatus according to claim 1, wherein the vessel further defines one or more divots in the bottom of the vessel.

12. An apparatus according to claim 11, wherein at least one of the one or more divots is dimensioned to capture the biological material within a small pocket within the intermediate restriction.

13. An apparatus according to claim 11, wherein the one or more divots comprise a first divot positioned near a start of the restriction and a second divot positioned at the middle of the restriction.

14. An apparatus according to claim 1, wherein a material of the vessel has a thickness between 1 mm and 0.05 mm.

* * * * *